United States Patent [19]

Yit Nieh

[11] Patent Number: 4,775,519

[45] Date of Patent: Oct. 4, 1988

[54] REMOVAL OF ACID GASES FROM GAS STREAMS

[75] Inventor: Edward C. Yit Nieh, Austin, Tex.

[73] Assignee: Texaco Inc., White Plains, N.Y.

[21] Appl. No.: 793,362

[22] Filed: Oct. 31, 1985

[51] Int. Cl.$^4$ .................. C01B 17/16; C01B 31/20

[52] U.S. Cl. .................... 423/226; 423/228; 423/229

[58] Field of Search ............ 423/229, 228, 226

[56] References Cited

U.S. PATENT DOCUMENTS 4,336,233  6/1982  Appl et al. .................. 423/226

*Primary Examiner*—John Doll
*Assistant Examiner*—Lori S. Freeman
*Attorney, Agent, or Firm*—Jack H. Park; Kenneth R. Priem; Carl G. Ries

[57] ABSTRACT

Improvement are provided in accordance with the present invention by a continuous process for the treating of a gas stream containing acid gas components wherein the gas stream is counter currently contacted in an absorption zone with an aqueous solution of a mixture of N-methyldiethanolamine with imidazole or a methyl substituted imidazole to thereby provide for acid gas (e.g., $CO_2$) absorption.

7 Claims, No Drawings

REMOVAL OF ACID GASES FROM GAS STREAMS

TECHNICAL FIELD OF THE INVENTION

This invention relates to a method for the bulk removal of acid gases such as $CO_2$, $H_2S$, etc. from a gas stream by absorption. More particularly, this invention is directed to a method wherein a gas stream, such as a synthesis gas stream, a natural gas stream comprising normally gaseous hydrocarbons, etc., is counter currently contacted in an absorption zone with a treating agent consisting essentially of an aqueous solution of N-methyldiethanolamine and imidazole and/or a methyl substituted imidazole to provide a gas stream containing a significantly reduced concentration of acid gas and to provide a rich absorption stream of treating agent containing acid gases absorbed from the gas stream and wherein the rich solution is depressured in order to flash at least a portion of the absorbed acid gases from the rich solution for recovery and to thereby provide a lean solution of N-methyldiethanolamine and imidazole and/or a methyl substituted imidazole for recycle to the absorption zone.

DESCRIPTION OF THE PRIOR ART

Appl et al. U. S. Pat. No. 4,336,233 discloses process for the removal of $CO_2$ and/or $H_2S$ from a gas stream by scrubbing the gas stream with an aqueous solution of methyldiethanolamine and piperazine.

French Pat. No. 2,100,475 is directed to a process for the selective absorption of sulfur-containing gases, especially sulfur dioxide and hydrogen sulfide. The patentees propose the use of a solvent for selective absorption which is a mixture of water with at least one nitrogen compound and, optionally, a polyoxyalkylene glycol or a monoalkyl ether of a polyoxyalkylene glycol. The patentees propose to use, as the nitrogen compound, materials such as alkoxylated amines (e.g., diethanolamine, N-methyldiethanolamine, etc.), alkoxylated alkylene polyamines (e.g., tetrahydroxyethylethylene diamine), nitrogen-containing heterocyclic compounds such as hydroxyethoxyethyl-morpholine, dihydroxyethyl-piperazine, hydroxyethylpiperidine, hydroxyethylpyrrole, hydroxyethylacetidine), etc.

H. D. Frazier, et al., in an article entitled "Selective Absorption of Hydrogen Sulfide from Gas Streams", Industrial and Engineering Chemistry, November, 1950, pgs. 2288-2292, disclose a selective process for the removal of hydrogen sulfide from a gas stream containing both hydrogen sulfide and carbon dioxide through the use of a solvent comprising an aqueous solution of N-methyldiethanolamine and diethylene glycol.

F. C. Vidaurri et al., in a paper presented at the 977 Gas Conditioning Conference, disclose the use of N-methyldiethanolamine for the purification of ethane.

The relative solubilities of hydrogen sulfide and carbon dioxide in aqueous solutions of N-methyldiethanolamine is reported in an article by Fang-Yuan Joe et al. entitled "Solubility of $H_2S$ and $CO_2$ in Aqueous Methyldiethanolamine Solutions" (*Ind. Eng. Chem. Process Des. Dev.*, Volume 21, No. 4, 1982, pgs. 539-544).

The use of "Sterically Hindered Amines for $CO_2$ Removal from Gases" has been disclosed by Sartori et al. (Ind. Eng. Chem. Fundam., 1983, 22, 239-249).

An article entitled "Purified $CO_2$ with a Low-Energy Process" (Meissner, Energy Progress, Volume 4, No. 1, March 1984, pgs. 17-21) describes a cyclic process for removing hydrogen sulfide from carbon dioxide streams to be used for enhanced crude oil recovery wherein the gas treating agent that is used is an aqueous solution of N-methyldiethanolamine with triethanolamine. A novel feature of the process described by Meissner is the regeneration of the rich solvent treating solution by flashing rather than by steam stripping.

The kinetics of the reaction of $CO_2$ with methyldiethanolamine is discussed by Barth et al. in an article entitled "Kinetics and Mechanisms of the Reactions of Carbon Dioxide with Alkanolamine: A Discussion Concerning the Cases of MDEA and DEA" (Chemical Engineering Science, Vol. 39 #12, pp. 1753-1757, 1984; printed in Great Britain).

The use of N-methyldiethanolamine in a continuous gas treating process involving counter current extraction of acid gases is disclosed in some detail in an article by Roland E. Meissner, III, presented at the 34th Annual Gas Conditioning Process and entitled "Reducing Gas Treating Plant Capital and Operating Costs".

BACKGROUND OF THE INVENTION

Many gas streams such as natural gas streams comprising normally gaseous hydrocarbons such as methane, ethane, propane, etc., synthesis gas streams, etc., are contaminated with sulfur-containing acid gases such as carbon dioxide, hydrogen sulfide, sulfur dioxide, mercaptans, etc. It is important to remove the acid gas impurities from such gas streams in order to enhance their utility and also to avoid environmental pollution. A commonly used method for removing acid gases is a solvent extraction process wherein a lean solvent which has absorption capacity for one or more of the acid gas contaminants is brought into counter current contact with a gas stream to be treated on a continuous basis in an absorption zone. The at least partially purified gas stream is discharged from the absorption zone for further processing or venting to the atmosphere while the solvent, rich in absorbed gases, is discharged from the absorption zone to a regeneration zone where the acid gases are removed from the rich solvent solution to thereby provide a lean solution of solvent for recycle to the absorption zone and a stream of desorbed sulfur-containing contaminants. Such a process is shown, for example in Appl et al. U.S. Pat. No. 4,336,233.

The desorbed stream of carbon dioxide can be used, for example, for enhanced oil recovery.

A wide variety of solvents have been proposed for processes of this nature, such as sulpholanes, alkanolamines, heterocyclic nitrogen-containing compounds such as piperazines and morpholines, etc. The particular solvent that is used in a particular situation is normally selected on the basis of the nature of the gas stream, the degree of contamination of the gas stream to be treated, the pressure of the gas stream and the downstream processing of the gas stream.

Aqueous N-methyl diethanolamine (MDEA) is a preferred gas treating agent for the bulk removal of carbon dioxide from natural gas, associative gas derived from carbon dioxide flooding, coke-oven gases and synthesis gases of any origin. The primary advantage of the MDEA based absorbent stems from the fact that aqueous MDEA can absorb as much as one mole of carbon dioxide per mole of amine whereas common aminoalcohols such as monoethanolamine, diethanolamine, $\beta,\beta'$-hydroxylaminoethyl ether and diisopropanolamine can absorb not much beyond 0.5 mole/mole of amine. Furthermore, under a high carbon dioxide loading condition, the aqueous MDEA absorbent can be regenerated by adiabatic flashing when pressure is reduced. These features contribute to the overall energy efficiency of gas treating processes based on aqueous MDEA.

The energy efficiency and equipment costs of gas treating processes can be further improved if the total amine concentration of the absorbent can be increased. A factor limiting how much MDEA concentration can be increased is that at a certain point any further increase in MDEA concentration will result in a counterproductive absorption rate decrease. The prior art discloses that morpholine, monomethyl ethanolamine and piperazines can be used to increase the total base in the MDEA based absorbent.

Although the results that have heretofore been obtained with N-methyldiethanolamine have been encouraging, they have not been entirely satisfactory and there is a need for improvement.

SUMMARY OF THE INVENTION

Improvements are provided in accordance with the present invention by a continuous process for the treating of a gas stream contaminated with acid gases wherein the gas stream is counter currently contacted in an absorption zone with an aqueous solution of N-methyldiethanolamine and imidazole or a methyl substituted imidazole to thereby provide for acid gas (e.g., $CO_2$) absorption. The gas stream which is thus treated, can be discharged from the absorption zone as a gas stream substantially depleted of acid gas for further downstream processing while the rich concentrated aqueous solution of a mixture of N-methyldiethanolamine with the imidazole can be discharged from the absorption zone for regeneration, all in accordance with known procedures.

In accordance with the preferred embodiment of the present invention, the desorption is accomplished by reducing the pressure on the rich concentrated solution of MDEA and the imidazole whereby the absorbed acid gas will flash from the solution to at least partially purify the same. One, or preferably a plurality of stages of flashing are incorporated in order to at least partially purify the concentrated aqueous solution of MDEA and the imidazole so that it can be recycled to the absorption zone.

DESCRIPTION OF THE PREFERRED EMBODIMENT

The starting materials for the preparation of the gas treating solution of the present invention are water, N-methyldiethanolamine and imidazole or a methyl-substituted imidazole (i.e., 1-methyl-imidazole, 2-methyl-imidazole or 4-methyl-imidazole).

The N-methyldiethanolamine will suitably be used in an amount such that the aqueous gas treating solution contains from about 40 wt. % to about 60 wt. % of N-methyldiethanolamine. A lesser amount of imidazole or of a methyl-substituted imidazole may suitably be used such that the aqueous gas treating solution contains from about 5 wt. % to about 15 wt. % of the imidazole.

When the gas stream to be treated contains a significant amount of $CO_2$, a preferred treating solution will consist essentially of an aqueous solution of N-methyldiethanolamine and imidazole in order to attain an enhanced rate of removal of the $CO_2$.

Treating conditions in the absorption zone may include, for example, a temperature of about 10° to about 70° C. and a pressure of about atmospheric to about 2000 psig.

The equipment to be used in the practice of the present invention may be of any suitable conventional construction, as disclosed for example, in the prior art mentioned above.

EXAMPLE OF PRACTICE OF THE PREFERRED PROCESS OF THE PRESENT INVENTION

By way of example, a feed gas may be derived from a natural gas well consisting essentially of hydrocarbons (e.g., methane) and contaminated with from about 30 to 50 wt. % of $CO_2$.

The gas may be fed to an absorption tower of conventional construction at a rate of about 200 cubic meters per hour.

At the same time a lean aqueous solution of N-methyldiethanolamine and imidazole containing about 50 wt. % of N-methyldiethanolamine and about 7 wt. % of imidazole may be charged to the top of the absorption tower at a temperature of about 50° C.

As a consequence, the gas fed to the absorption tower will be significantly purified such that the treated gas leaving the absorption zone will contain not more than about 2 wt. % of $CO_2$.

EXAMPLES

The invention will be further illustrated by the following specific examples which are given by way of illustration and not as limitations on the scope of this invention.

EXAMPLE 1

In order to demonstrate the efficacy of the present invention, for the selective removal of carbon dioxide, a number of experiments were performed in a specially designed apparatus.

The apparatus comprised a thermostated autoclave equipped with gauges, a pressure transducer, Validyne model CD23 and an adjustable speed stirrer containing 250 ml of the absorbing agent to be tested and was stirred at 450 rpm rate and evacuated to 24 inches of Hg vacuum. A sample of carbon dioxide, 3785 ml at 67 psig. was allowed to expand at reaction temperature into the thermostated vapor space of the evaporated autoclave while minimizing the disturbance of the vapor liquid interface. The absorption rate was then determined from the subsequent pressure drop which results from carbon dioxide being absorbed into the test solution. The pressure drop was recorded on a strip chart recorder. The observed first order rate constant was calculated by the method of Guggenheim (E. A. Guggenheim, *Phil. Mag.*, 1, 538 (1926)) from the pressure time plot covering four to five half lives of the reaction. The results of Examples 1–42 are listed in Tables I and II.

TABLE I

Carbon Dioxide Absorption Rates at 40° C.[a]

| Example | Additive | Grams | N | Total[b] Base N | kobsd psig/hr | Half Life, Hours |
|---|---|---|---|---|---|---|
| 1 | None | — | — | 3.26 | 0.237 | 2.92 |
| 2 | MDEA | 9.2 | 0.31 | 3.57 | 0.227 | 3.05 |
| 3 | MDEA | 18.4 | 0.62 | 3.88 | 0.217 | 3.19 |
| 4 | MDEA | 27.6 | 0.93 | 4.19 | 0.201 | 3.45 |
| 5 | MDEA | 36.8 | 1.24 | 4.50 | 0.179 | 3.87 |
| 6 | Piperazine | 3.3 | 0.31 | 3.57 | 0.244 | 2.84 |
| 7 | Piperazine | 6.6 | 0.62 | 3.88 | 0.239 | 2.90 |
| 8 | Piperazine | 9.9 | 0.93 | 4.19 | 0.218 | 3.18 |
| 9 | Piperazine | 13.2 | 1.24 | 4.50 | 0.206 | 3.36 |
| 10 | Imidazole | 2.8 | 0.31 | 3.57 | 0.225 | 3.08 |
| 11 | Imidazole | 5.6 | 0.62 | 3.88 | 0.222 | 3.12 |
| 12 | Imidazole | 8.4 | 0.93 | 4.19 | 0.225 | 3.08 |
| 13 | Imidazole | 11.2 | 1.24 | 4.50 | 0.238 | 2.91 |
| 14 | Imidazole | 14.0 | 1.55 | 4.81 | 0.237 | 2.92 |
| 15 | 1-Methyl Imidazole | | 0.31 | 3.57 | 0.216 | 3.21 |
| 16 | 1-Methyl Imidazole | | 0.62 | 3.88 | 0.239 | 2.89 |
| 17 | 1-Methyl Imidazole | | 0.93 | 4.16 | 0.233 | 2.97 |
| 18 | 1-Methyl Imidazole | | 1.24 | 4.50 | 0.191 | 3.62 |
| 19 | 2-Methyl Imidazole | | 0.31 | 3.57 | 0.239 | 2.90 |
| 20 | 2-Methyl Imidazole | | 0.62 | 3.88 | 0.224 | 3.09 |
| 21 | 2-Methyl Imidazole | | 0.93 | 4.16 | 0.212 | 3.26 |
| 22 | 2-Methyl Imidazole | | 1.24 | 4.50 | 0.200 | 3.47 |

[a] Experiments were carried out using 3.26 N aqueous MDEA promoted with additive as noted in the table.
[b] Total base is the sum of the normality of the additive and the normality of the aqueous MDEA solution.

TABLE II

Carbon Dioxide Absorption Rates at 20° C.[a]

| Example | Additive | Grams | N | Total[b] Base N | kobsd psig/hr | Half Life, Hours |
|---|---|---|---|---|---|---|
| 23 | None | — | — | 3.26 | 0.132 | 5.25 |
| 24 | MDEA | 9.2 | 0.31 | 3.57 | 0.111 | 6.24 |
| 25 | MDEA | 18.4 | 0.62 | 3.88 | 0.093 | 7.41 |
| 26 | MDEA | 27.6 | 0.93 | 4.19 | 0.081 | 8.56 |
| 27 | MDEA | 36.8 | 1.24 | 4.50 | 0.069 | 10.04 |
| 28 | Piperazine | 3.3 | 0.31 | 3.57 | 0.144 | 4.81 |
| 29 | Piperazine | 6.6 | 0.62 | 3.88 | 0.133 | 5.29 |
| 30 | Piperazine | 9.9 | 0.93 | 4.19 | 0.121 | 5.72 |
| 31 | Piperazine | 13.2 | 1.24 | 4.50 | 0.118 | 5.87 |
| 32 | Imidazole | 2.8 | 0.31 | 3.57 | 0.140 | 4.95 |
| 33 | Imidazole | 5.6 | 0.62 | 3.88 | 0.136 | 5.09 |
| 34 | Imidazole | 8.4 | 0.93 | 4.19 | 0.136 | 5.09 |
| 35 | Imidazole | 11.2 | 1.24 | 4.50 | 0.158 | 4.39 |
| 36 | 1-Methyl Imidazole | | 0.31 | 3.57 | 0.137 | 5.04 |
| 37 | 1-Methyl Imidazole | | 0.62 | 3.88 | 0.143 | 4.85 |
| 38 | 1-Methyl Imidazole | | 0.93 | 4.16 | 0.159 | 4.35 |
| 39 | 2-Methyl Imidazole | | 0.31 | 3.57 | 0.129 | 5.37 |
| 40 | 2-Methyl Imidazole | | 0.62 | 3.88 | 0.113 | 6.13 |
| 41 | 2-Methyl Imidazole | | 0.93 | 4.16 | 0.103 | 6.73 |
| 42 | 2-Methyl Imidazole | | 1.24 | 4.50 | 0.104 | 6.67 |

[a] Experiments were carried out using 3.26 N aqueous MDEA promoted with additive as noted in the table.
[b] Total base is the sum of the normality of the additive and the normality of the aqueous MDEA solution.

Note from Tables I and II that imidazole and the methyl-substituted imidazoles were effective for the absorption of $CO_2$, being at least about as effective as piperazine at the lower concentrations where the total base was about 3.57 and about 3.88 and, in the case of imidazole, being more effective than piperazine at higher concentrations where, for example, the total base was about 4.19 and about 4.50.

What is claimed is:

1. In a method for the purification of a stream of gas comprising a normally gaseous hydrocarbon or synthesis gas contaminated with acid gases which comprises the steps of:

countercurrently contacting said gas stream in an absorption zone with a stream of a treating agent consisting essentially of an aqueous solution of N-methyldiethanolamine and imidazole or a methyl substituted imidazole to thereby remove a substantial portion of the acid contaminants from said hydrocarbon gas stream by absorption into said treating agent, discharging an at least partially purified gas stream from said absorption zone, discharging said treating agent enriched with absorbed acid gas components from said absorption zone; and subsequently regenerating said enriched treating agent.

2. A method as in claim 1, wherein the said aqueous solution contains from about 40 to about 60 wt. % of N-methyldiethanolamine and from about 5 to about 15 wt. % of imidazole and/or a methyl substituted imidazole.

3. A method as in claim 2, wherein the conditions utilized in said absorption zone include a temperature within the range of about 10° to about 70° C. and a pressure of from about atmospheric to about 2000 psig.

4. A method as in claim 3, wherein the aqueous solution consists essentially of water, N-methyldiethanolamine and imidazole.

5. A method as in claim 3, wherein the aqueous solution consists essentially of water, N-methyldiethanolamine and 1-methyl imidazole.

6. A method as in claim 3, wherein the aqueous solution consists essentially of water, N-methyldiethanolamine and 2-methyl imidazole.

7. A method as in claim 3, wherein the aqueous solution consists essentially of water, N-methyldiethanolamine and 4-methyl-imidazole.

* * * * *